(12) United States Patent
Atwell

(10) Patent No.: US 10,507,031 B2
(45) Date of Patent: Dec. 17, 2019

(54) TISSUE BAG AND METHOD OF REMOVING EXCISED TISSUE

(71) Applicant: Gyrus Medical Limited, Cardiff (GB)

(72) Inventor: Tony Atwell, Wales (GB)

(73) Assignee: Gyrus Medical Limited, Cardiff (GB)

( * ) Notice: Subject to any disclaimer, the term of this patent is extended or adjusted under 35 U.S.C. 154(b) by 289 days.

(21) Appl. No.: 15/497,800

(22) Filed: Apr. 26, 2017

(65) Prior Publication Data

US 2017/0333061 A1 Nov. 23, 2017

(30) Foreign Application Priority Data

May 20, 2016 (GB) .................................. 1608910.4

(51) Int. Cl.
*A61B 17/221* (2006.01)
*A61B 10/04* (2006.01)
*A61B 17/00* (2006.01)

(52) U.S. Cl.
CPC ............ *A61B 17/221* (2013.01); *A61B 10/04* (2013.01); *A61B 2017/00287* (2013.01); *A61B 2017/00296* (2013.01)

(58) Field of Classification Search
CPC . A61B 10/04; A61B 17/22031; A61B 17/221; A61B 2017/2212; A61B 2017/2215; A61B 2017/00287; A61B 2017/00296; A61B 2017/00738; A61B 2017/22034; A61B 2217/005
See application file for complete search history.

(56) References Cited

U.S. PATENT DOCUMENTS

| 5,037,379 A | 8/1991 | Clayman et al. |
| 5,190,555 A | 3/1993 | Wetter et al. |
| 5,312,416 A | 5/1994 | Spaeth et al. |
| 5,341,815 A | 8/1994 | Cofone et al. |

(Continued)

FOREIGN PATENT DOCUMENTS

| DE | 4242153 A1 | 6/1994 |
| EP | 1679040 A1 | 7/2006 |

(Continued)

OTHER PUBLICATIONS

Judge, T., "UK Combined Search and Examination Report", prepared for application No. 1706547.5, dated Sep. 29, 2017, 9 pages.

(Continued)

*Primary Examiner* — Jocelin C Tanner
(74) *Attorney, Agent, or Firm* — Winstead PC

(57) ABSTRACT

A surgical tissue bag (7) for use in the removal of tissue from a surgical site comprises an elongate handle (8) having a proximal portion (15) and a distal portion (14), and a pouch (9) disposed at the end of the handle. The pouch (9) comprises a flexible ring (10) and a bag portion (11) depending from the ring and forming an enclosure to contain tissue and other fluid material. The handle (8) includes an offset portion (13) such that the distal portion (14) is offset from the proximal portion (15) by a discrete amount. The proximal portion of the handle forms a longitudinal axis, and the ring (10) forms a plane at an angle to the longitudinal axis. The bag portion (11) is shaped such that it defines a bag longitudinal axis, the bag longitudinal axis being non-orthogonal to the plane of the ring (10).

14 Claims, 3 Drawing Sheets

(56) References Cited

U.S. PATENT DOCUMENTS

| | | | | |
|---|---|---|---|---|
| 5,368,597 | A | * | 11/1994 | Pagedas ............ A61B 17/00234 600/37 |
| 8,734,464 | B2 | * | 5/2014 | Grover .................. A61B 17/00 606/114 |
| 2003/0163129 | A1 | * | 8/2003 | Lee ...................... A61B 8/0825 606/47 |
| 2004/0059345 | A1 | * | 3/2004 | Nakao .................. A61B 17/221 606/113 |
| 2011/0076451 | A1 | * | 3/2011 | Mekaru ................ B29C 59/022 428/141 |
| 2011/0087235 | A1 | * | 4/2011 | Taylor .............. A61B 17/00234 606/114 |
| 2011/0190782 | A1 | * | 8/2011 | Fleming ........... A61B 17/00234 606/114 |

FOREIGN PATENT DOCUMENTS

| | | |
|---|---|---|
| EP | 2353511 A1 | 8/2011 |
| EP | 2594205 A1 | 5/2013 |
| WO | WO-92/16156 A1 | 10/1992 |
| WO | WO-03/022157 A2 | 3/2003 |

OTHER PUBLICATIONS

Alexander, R., "UK Search Report", prepared for application No. 1608910.4, dated Nov. 21, 2016, 4 pages.

\* cited by examiner

TISSUE BAG AND METHOD OF REMOVING EXCISED TISSUE

BACKGROUND OF THE INVENTION

This invention relates to a tissue bag for use in the encapsulation of tissue, and to a method for removing excised tissue such as resected bladder tumours. Due to the perceived risks associated with the "seeding" of cancerous tissue, the morcellation of tissue is often carried out in a tissue bag surrounding or containing the tissue. An example of such a tissue bag is given in U.S. Pat. No. 5,037,379. In the tissue bag of U.S. Pat. No. 5,037,379, a morcellating instrument is introduced into the bag in order to morcellate the tissue into smaller pieces before the bag is removed from the body of the patient. However, a tissue bag is not generally used when resected tissue is being removed from the patient.

SUMMARY OF THE INVENTION

The present invention attempts to provide a tissue bag suitable for use when resected tissue is being removed from a patient. Accordingly, a surgical tissue bag for use in the removal of tissue from a surgical site comprises an elongate handle having a proximal portion and a distal portion, and a pouch disposed at the end of the handle, the pouch comprising a flexible ring and a bag portion depending from the ring and forming an enclosure to contain tissue and other fluid material, the handle including an offset portion such that the distal portion is offset from the proximal portion by a discrete amount.

This discrete amount allows for the alignment of the bag opening with a tissue grasper deployed through another working channel of the same endoscope. Conveniently, the discrete amount by which the distal portion is offset from the proximal portion is between 0.1 and 0.5 times the diameter of the ring, and typically by between 0.2 and 0.3 times the diameter of the ring.

Conveniently, the proximal portion of the handle forms a longitudinal axis, and the ring forms a plane at an angle to the longitudinal axis.

The ring preferably forms a plane at an angle of between 30 and 60 degrees to the longitudinal axis of the handle, conveniently between 40 and 50 degrees, and typically approximately 45 degrees to the longitudinal axis of the handle. Conveniently, the bag portion is shaped such that it defines a bag longitudinal axis, the bag longitudinal axis being non-orthogonal to the plane of the ring. Typically, the surgical tissue bag is deployed through the working channel of an endoscope. By making the longitudinal bag axis non-orthogonal to the plane of the ring, it is easier to insert tissue into the bag using a tissue grasper deployed through another working channel of the same endoscope. To achieve this, the bag longitudinal axis is preferably parallel to the longitudinal axis of the handle.

Preferably, the bag longitudinal axis is coaxial with the longitudinal axis of the handle. This aligns the opening of the tissue bag with the handle such that the bag is in position to receive tissue being moved along the longitudinal axis of the handle. Typically, the bag portion has parallel sides, and conveniently the sides of the bag portion are parallel with the longitudinal axis of the handle.

The handle typically comprises a wire, or alternatively a flexible shaft. Either way, the handle can be used to manoeuvre the tissue bag into position within the patient. The tissue bag can be used to enclose excised tissue which is being removed from a patient, such that it is not exposed to the patient's body during removal. For example, when an excised bladder tumour is being removed through the patient's urethra, it is enclosed within the tissue bag as opposed to being exposed to the walls of the urethra. Conceivably, the tissue bag may also include a suction tube extending into the bag portion, helping to remove fluid material from within the bag portion. The tissue bag may contain fluid and other material that may hinder the collapsing of the bag as it is being withdrawn, and the suction tube evacuates this fluid without allowing it to come into contact with the patient as the endoscope is being withdrawn.

The invention further resides in a combination comprising an endoscope, a tissue grasper and a tissue retrieval bag, the endoscope including at least two working channels, one for the tissue grasper and one for the tissue retrieval bag, the tissue retrieval bag comprising an handle having a proximal end and a distal end and defining a longitudinal axis, and a pouch disposed at the end of the handle, the pouch comprising a flexible ring and a bag portion depending from the ring and forming an enclosure, the handle including an offset portion such that the distal portion is offset from the proximal portion by a discrete amount, such that when the tissue grasper is moved distally within its working channel the distal end of the tissue grasper passes through the ring and is received within the enclosure. The combination conceivably further includes a suction tube extending into the bag portion, helping to remove fluid material from within the bag portion.

The invention further resides in a method of surgically removing excised tissue from a surgical site within the body of a patient, the method comprising the steps of
i) introducing an endoscope into the surgical site,
ii) introducing a tissue grasper through a working channel of the endoscope,
iii) grasping the excised tissue with the tissue grasper,
iv) retracting the tissue grasper such that the excised tissue is adjacent the distal end of the endoscope,
v) introducing a tissue retrieval bag through another working channel of the endoscope such that it is distal of the excised tissue,
vi) moving the tissue grasper distally such that the excised tissue is received within the tissue retrieval bag,
vii) operating the tissue grasper to release the excised tissue within the tissue retrieval bag,
viii) withdrawing the tissue grasper from the surgical site through the working channel of the endoscope,
ix) withdrawing the tissue retrieval bag such that it is at least partly received within the working channel of the endoscope, such that the contents of the bag are sealed against egress, and
x) withdrawing the endoscope from the surgical site pulling the tissue retrieval bag and the excised tissue therewith.

The method conceivably also includes the additional step of suctioning fluid material from the tissue retrieval bag before the endoscope is withdrawn from the surgical site.

BRIEF DESCRIPTION OF THE DRAWINGS

The invention will now be further described, by way of example only, with reference to the accompanying drawings, in which.

DETAILED DESCRIPTION OF EXEMPLARY EMBODIMENTS

Figure 1:
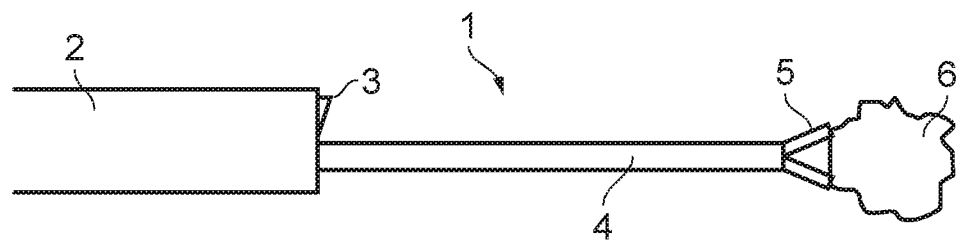
FIG. 1 is a schematic side view of an endoscopic tissue grasper being introduced into a surgical site.

Referring to FIG. 1, a surgical site is shown generally at 1, with an endoscope 2 introduced into the surgical site 1. Typically, the surgical site is a human bladder, with the endoscope 2 being introduced into the bladder via the urethra (not shown). The endoscope 2 contains a telescope or camera shown at 3 and a tissue grasper 4 present within one of the working channels (not shown) of the endoscope. The tissue grasper has a pair of jaws 5 which are shown in FIG. 1 as grasping tissue 6, such as an excised bladder tumour. The surgical site 1 contains a fluid such as saline (again not shown).

Figure 2:
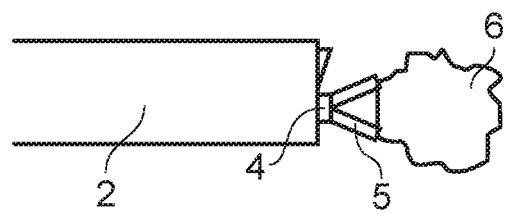
FIG. 2 is a schematic side view of the tissue grasper of FIG. 1 being moved to a position adjacent the endoscope.
Figure 3:
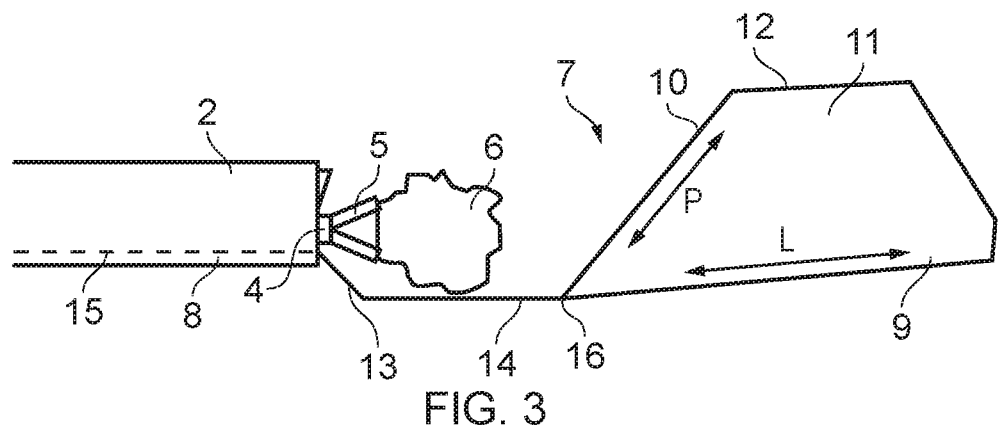
FIG. 3 is a schematic side view showing a tissue bag in accordance with the present invention being deployed through the endoscope.

Once the tissue 6 has been grasped by the jaws 5, the tissue grasper 4 is withdrawn so that the tissue 6 is adjacent the distal end of the endoscope 2, as shown in FIG. 2. FIG. 3 shows a tissue bag 7 being deployed from another working channel of the endoscope 2, the tissue bag comprising a wire handle 8, and a pouch 9 at the distal end of the handle 8. The pouch comprises a wire ring 10, and a bag portion 11 depending from the wire ring 10. The bag portion 11 is formed of an impervious, polymeric material, and comprises a cylindrical sidewall 12 defining a bag longitudinal axis "L". The bag longitudinal axis "L" is non-orthogonal to the plane "P" of the ring 10, such that it defines an angle of 45 degrees thereto.

Figure 4:
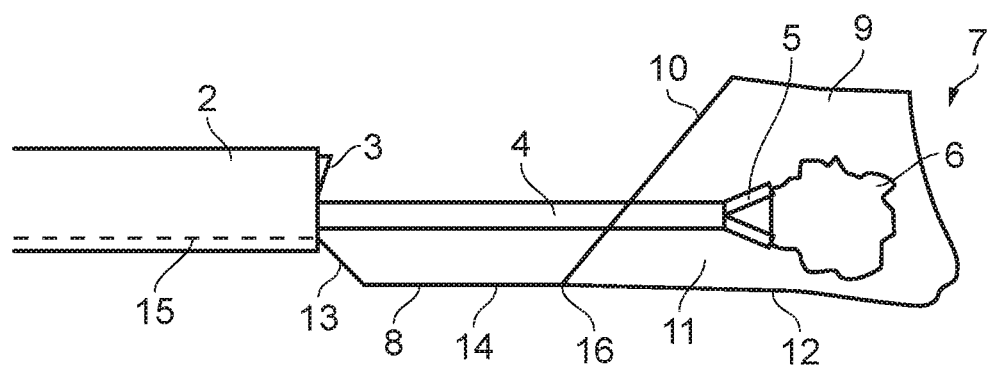
FIG. 4 is a schematic side view showing the tissue grasper of FIG. 1 placing tissue into the tissue bag of FIG. 3.

The handle 8 includes an angled portion 13, such that the distal portion 14 of the handle is offset from the proximal portion 15 of the handle. This offset ensures that when the tissue bag 7 is deployed from the endoscope 2, the lower extremity 16 of the wire ring 10 sits at a position below the endoscope 2. With the offset handle, and the angle of the wire ring 10, the tissue bag is designed such that once it has been deployed, movement of the tissue grasper 4 distally causes the jaws 5 (and hence the tissue 6) to be received within the pouch 9, as shown in FIG. 4.

Figure 5:
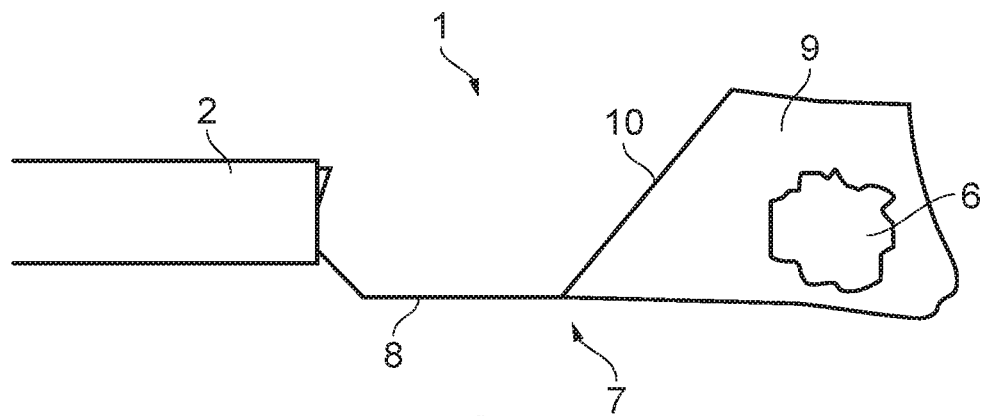
FIG. 5 is a schematic side view showing tissue within the tissue bag of FIG. 3.
Figure 6:
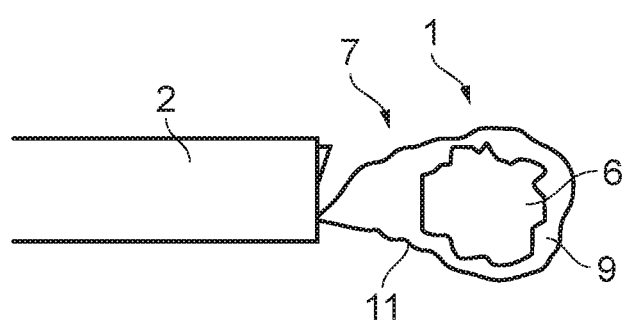
FIG. 6 is a schematic side view showing the tissue bag of FIG. 3 being moved to a position adjacent the endoscope.

Once the tissue 6 is located within the pouch 9, the tissue grasper is operated to release the tissue, and the tissue grasper 4 is withdrawn through the working channel of the endoscope 2, leaving the tissue 6 within the pouch 9, as shown in FIG. 5. The handle 8 is then used to withdraw the tissue bag 7 towards the endoscope 2, as shown in FIG. 6. As the tissue bag 7 is withdrawn, the wire ring 10 starts to be received within the working channel of the endoscope, and the bag portion 11 starts to collapse. Any saline or other fluid contained within the bag portion is withdrawn through the working channel of the endoscope, rather than being expelled into the surgical site 1. The working channel of the endoscope 2 may be provided with suction, in order to assist in the evacuation of fluid from within the bag portion 11.

Figure 7:
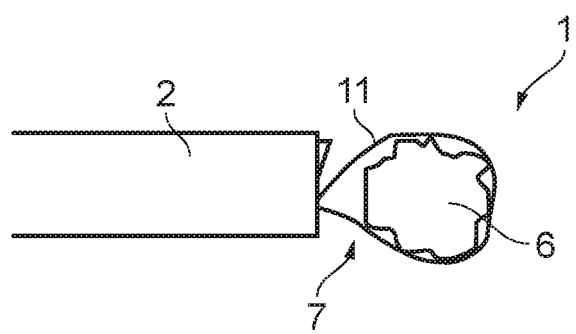
FIG. 7 is a schematic side view showing the endoscope being withdrawn from the surgical site.

FIG. 7 shows the bag portion 11 collapsed around the tissue 6, with the wire ring 10 completely received within the working channel of the endoscope, and with the contents of the bag portion 11 completely sealed from the surgical site 1. When the tissue bag 7 is in this condition, the endoscope 2 can be withdrawn from the surgical site 1, for example through the urethra. While the endoscope 2 is being withdrawn in this way, the bag portion 11 seals the excised tissue 6 and any other contents of the bag portion from contact with the urethra, thereby preventing any seeding or contamination of the patient from the contents of the tissue bag 7.

Figure 8:
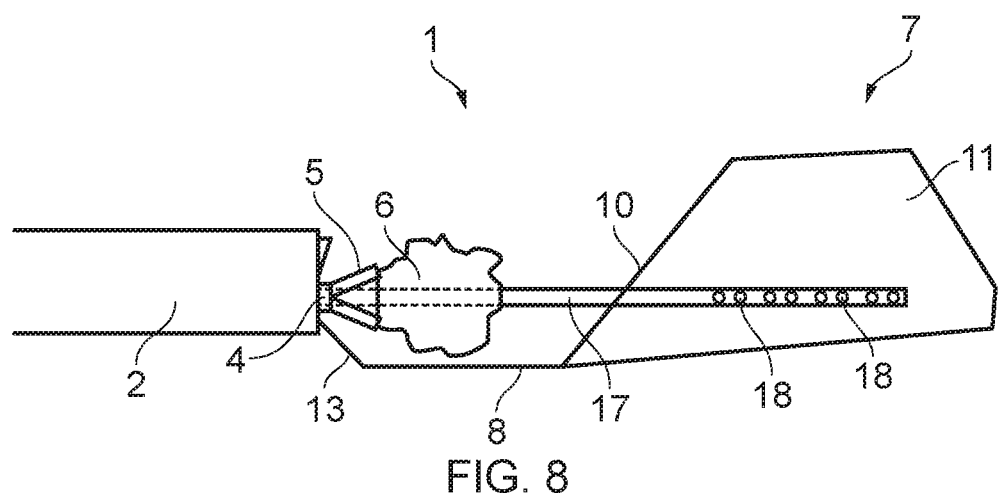
FIG. 8 is a schematic side view of an alternative embodiment of tissue bag in accordance with the present invention being deployed through an endoscope.

FIG. 8 shows an alternative embodiment of tissue bag 7 deployed from an endoscope 2 in an equivalent position to that of FIG. 3. The tissue grasper 4 is grasping tissue 6, and the angled portion 13 of the handle 8 allows the tissue bag to be deployed past the grasper 4. However, in the embodiment of FIG. 8, the tissue bag 7 is provided with a suction tube 17 which is deployed with the bag and extends into the bag portion 11. The suction tube 17 has suction apertures 18 towards its distal end, and the proximal end of the suction tube is connected to a source of suction (not shown).

Figure 9:
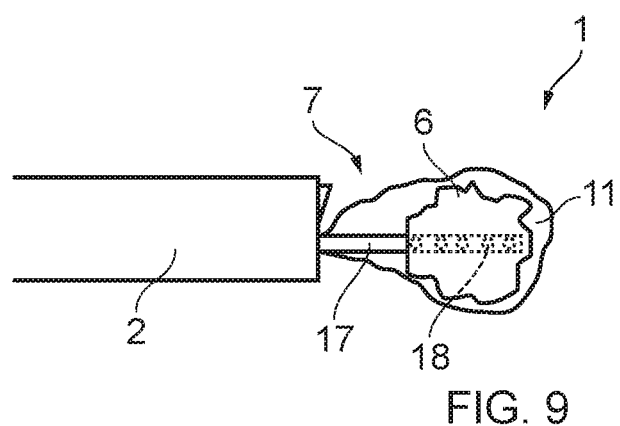
FIG. 9 is a schematic side view showing the tissue bag of FIG. 8 being moved to a position adjacent the endoscope.

FIG. 9 shows the arrangement when the tissue 6 has been placed into the bag portion 11 and the tissue grasper 4 withdrawn through the endoscope 2. In FIG. 9 the tissue bag 7 has been withdrawn towards the endoscope 2, similar to the arrangement shown in FIG. 6. When the source of suction is activated, fluid material within the bag portion is evacuated through the apertures 18 and along the suction tube 17 to exit the surgical site 1. This assists the bag portion 11 in collapsing around the tissue 6, and ensures that the tissue bag is not kept inflated by fluid within the bag portion 11. The fluid exits through the suction tube 17 as opposed to being expelled back into the surgical site when the bag portion collapses. As before, the endoscope 2 can be withdrawn from the surgical site 1, with the tissue 6 completely encapsulated by the bag portion 11.

Other embodiments will be apparent to those skilled in the art without departing from the scope of the present invention. For example, various shapes of bag portion 11 can be employed, and different angles for the wire ring 10 can be used also. However, the design of the tissue bag is such that it can be deployed past a tissue grasper holding tissue as shown in FIG. 3, and that the subsequent longitudinal movement of the tissue grasper places the tissue in the bag as shown in FIG. 4. In this way, simple distal/proximal movements of the bag and tissue grasper are all that is required, with complicated lateral movements or other manoeuvring of the grasper or tissue bag being unnecessary.

What is claimed is:

1. A tissue removal system comprising:
   an endoscope comprising a longitudinal axis that extends along a length of the endoscope;
   a tissue grasper disposed within a first working channel of the endoscope;
   a tissue retrieval bag disposed within a second working channel of the endo scope, the tissue retrieval bag comprising:
     a handle having a proximal portion and a distal portion; and
     a pouch disposed at the distal portion of the handle and comprising a flexible ring attached to the pouch, the flexible ring being attached to the handle at an angle such that the flexible ring transects a longitudinal axis of the handle;

wherein the proximal portion of the handle is offset a discrete amount from the longitudinal axis of the endoscope such that, when the tissue grasper is moved distally within the second working channel, a distal end of the tissue grasper passes through the flexible ring and is received within the pouch.

2. The tissue removal system of claim 1, wherein the discrete amount is between 0.1 and 0.5 times a diameter of the flexible ring.

3. The tissue removal system of claim 2, wherein the discrete amount is offset from the proximal portion is between 0.2 and 0.3 times a diameter of the flexible ring.

4. The tissue removal system of claim 1, wherein the flexible ring forms a plane at an angle of between 30 and 60 degrees to the longitudinal axis of the handle.

5. The tissue removal system of claim 4, wherein the flexible ring forms a plane at an angle of between 40 and 50 degrees to the longitudinal axis of the handle.

6. The tissue removal system of claim 5, wherein the flexible ring forms a plane at an angle of approximately 45 degrees to the longitudinal axis of the handle.

7. The tissue removal system of claim 1, wherein the pouch is shaped such that it defines a bag longitudinal axis, the bag longitudinal axis being non-orthogonal to a plane formed by the flexible ring.

8. The tissue removal system of claim 7, wherein the bag longitudinal axis is parallel to the longitudinal axis of the handle.

9. The tissue removal system of claim 8, wherein the bag longitudinal axis is coaxial with the longitudinal axis of the handle.

10. The tissue removal system of claim 1, wherein the pouch has parallel sides.

11. The tissue removal system of claim 10, wherein the parallel sides of the pouch are parallel with the longitudinal axis of the handle.

12. The tissue removal system of claim 1, wherein the handle comprises a wire.

13. The tissue removal system of claim 12, wherein the handle comprises a flexible shaft.

14. The tissue removal system of claim 1, wherein the endoscope comprises a suction tube configured to extend into the pouch to remove a fluid material from within the pouch.

* * * * *